United States Patent
Wada et al.

(10) Patent No.: US 8,779,785 B2
(45) Date of Patent: *Jul. 15, 2014

(54) WATER CONTENT DETECTION SENSOR

(75) Inventors: Ichiro Wada, Kagawa (JP); Miou Suzuki, Kagawa (JP); Kiyoshi Toda, Kagawa (JP); Yuichi Hirai, Tokyo (JP); Masaho Hayashi, Tokyo (JP); Hiroshi Uematsu, Tokyo (JP); Toshihiko Uenishi, Fukuoka (JP)

(73) Assignee: Unicharm Corporation, Ehime (JP)

( * ) Notice: Subject to any disclaimer, the term of this patent is extended or adjusted under 35 U.S.C. 154(b) by 159 days.

This patent is subject to a terminal disclaimer.

(21) Appl. No.: 13/365,292

(22) Filed: Feb. 3, 2012

(65) Prior Publication Data
US 2012/0200310 A1 Aug. 9, 2012

Related U.S. Application Data

(63) Continuation of application No. 11/988,781, filed as application No. PCT/JP2006/314052 on Jul. 14, 2006, now Pat. No. 8,183,876.

(30) Foreign Application Priority Data

Jul. 14, 2005 (JP) .................................. 2005-205974
Jun. 29, 2006 (JP) ............................... 20069-180319

(51) Int. Cl.
*G01N 27/04* (2006.01)
(52) U.S. Cl.
USPC ........................................................ 324/694
(58) Field of Classification Search
USPC ........................................................ 324/694
See application file for complete search history.

(56) References Cited

U.S. PATENT DOCUMENTS

| | | | |
|---|---|---|---|
| 3,356,979 A | 12/1967 | Bouyoucos | |
| 4,121,007 A | 10/1978 | Kobayashi et al. | |
| 4,523,142 A | 6/1985 | Murata et al. | |
| 4,972,179 A | 11/1990 | Akiba | |
| 5,619,144 A | 4/1997 | Stormborn | |
| 6,637,257 B2 | 10/2003 | Sparks | |
| 6,906,534 B2 | 6/2005 | Hoisington et al. | |
| 7,755,497 B2 * | 7/2010 | Wada et al. | 340/604 |
| 7,892,488 B2 | 2/2011 | Speldrich et al. | |

(Continued)

FOREIGN PATENT DOCUMENTS

| | | |
|---|---|---|
| JP | 63-290950 | 11/1988 |
| JP | 3-2653 | 1/1991 |

(Continued)

*Primary Examiner* — Reena Aurora
(74) *Attorney, Agent, or Firm* — Brinks Gilson & Lione

(57) ABSTRACT

A water content detection sensor includes a circuit member in which low resistance conductors disposed in parallel to each other and a high resistance conductor connecting end portions of the respective low resistance conductors, a carrier body having a water-proof property and an insulating property, and a coating body having a water-proof property and an insulating property, the circuit portion being disposed between the carrier body and the coating body. A plurality of exposure holes is provided which expose the low resistance conductors at plural portions. When water content adheres between the exposure holes and the low resistance conductors are then short-circuited and a current value is made larger than that before the adhesion of the water content. When a small current passes, it is judged that the circuit is normal, and on the other hand, a large current passes, it is judged that water is generated.

10 Claims, 7 Drawing Sheets

(56) References Cited

U.S. PATENT DOCUMENTS

| | | | |
|---|---|---|---|
| 8,183,876 B2 * | 5/2012 | Wada et al. | 324/694 |
| 2004/0032369 A1 | 2/2004 | Flowers | |
| 2004/0247889 A1 | 12/2004 | Nakajima et al. | |
| 2005/0184851 A1 | 8/2005 | Nelson | |
| 2005/0223827 A1 | 10/2005 | Walker | |

FOREIGN PATENT DOCUMENTS

| | | |
|---|---|---|
| JP | 2000-19136 | 1/2000 |
| JP | 2000-93448 | 4/2000 |
| JP | 2002-82080 | 3/2002 |
| JP | 2004-177120 | 6/2004 |

* cited by examiner

WATER CONTENT DETECTION SENSOR

RELATED APPLICATION

This application is a continuation of U.S. patent application Ser. No. 11/988,781 filed Jan. 26, 2009, now U.S. Pat. No. 8,183,876, which was a 35 U.S.C. §371 national phase filing of International Patent Application No. PCT/JP2006/314052, filed Jul. 14, 2006, through which and to which priority is claimed under 35 U.S.C. §119 to Japanese Patent Application Nos. 2005-205974, filed Jul. 14, 2005 and 2006-180319, filed Jun. 29, 2006. Priority claimed under 35 U.S.C. §120 to U.S. patent application Ser. No. 11/988,781 and under 35 U.S.C. §119 to Japanese Patent Application Nos. 2005-205974 and 2006-180319.

TECHNICAL FIELD

The present invention relates to a water content (or merely water) detection sensor.

BACKGROUND ART

Generally, there is known a water content detection sensor for detecting presence or generation of water content or moisture at a time when the water content or water adheres between electrodes and electric current passes (Such water content detection sensors are disclosed, for example, in Patent Literature1, 2, 3.). Such water content detection sensors are utilized for automatic wipers of automobiles, diapers and so on.

Patent Literature 1: JP-63-290950
Patent Literature 2: JP-2000-19136
Patent Literature 3: JP-2002-82080

DISCLOSURE OF THE INVENTION

Problems to be Solved by the Invention

In the water content detection sensor of the structure described in the above prior art references, for example, under the presence of a potential difference between the electrodes, when an electric current passes upon adherence of the water content between the electrodes, a signal is generated by the detection of the current and an output signal is then detected. In such structure, however, the performance of a circuit itself including the electrodes could not be judged, and it is therefore impossible to detect the generation or presence of the water content or water at the time of adhesion of the water content between the electrodes because of no generation of any signal due to fault of the circuit such as electrodes.

Furthermore, a conventional water content detection sensor is also utilized for diapers for detecting urination or evacuation. In such a case, when it is desired to detect the urination through plural times, resistance values may be changed, which results in a cause of erroneous operation of the detector.

Accordingly, the present invention was conceived in consideration of the circumstances mentioned above and an object of the present invention is to provide a water content detection sensor capable of surely detecting the presence of water content or water between electrodes.

Means for Solving the Problems

The above and other objects can be achieved according to the present invention by providing a water content detection sensor comprising: a circuit member in which low resistance conductors (1,2) disposed in parallel to each other and a high resistance conductor (3) connecting end portions of the respective low resistance conductors (1,2) so as to provide a series of line; a carrier body (4) having a water-proof property and an insulating property; and a coating body (5) having a water-proof property and an insulating property, the circuit member being disposed between the carrier body (4) and the coating body (5), wherein a plurality of exposure holes (6) are formed to the carrier body (4) or the coating body (5) so that the low resistance conductors (1,2) are exposed at plural portions, and when water content (W) adheres between the exposure holes (6) and the low resistance conductors (1,2) are then short-circuited in a current conduction state, a current value is made larger than that before the water content (W) adheres.

In a preferred embodiment of the above aspect of the present invention, the low resistance conductors (1,2) and the high resistance conductor (3) may be formed by being printed on the carrier body (4) in form of film and the coating body (5) is printed thereon.

Portions of the low resistance conductors (1,2) corresponding to the exposure holes (6) may be formed as enlarged portions (6a) each having an area larger than that of the exposure hole (6).

Extending portions (1a,2a) of the low resistance conductors (1,2) and the exposure holes (6) may be formed to portions at which the water content (W) is likely concentrated.

The carrier body (4) and the coating body (5) may be formed with through holes (9a,9b) through which water passes.

The low resistance conductors and the high resistance conductor may be printed with conductive ink including conductive carbon.

It may be desired that the printing ink of the low resistance conductor includes the conductive carbon of an amount larger than that included in the printing ink of the high resistance conductor.

The coating body or the carrier body, to which the exposure holes are formed, may be formed as a lamination member composed of printing ink layers, and at least one layer of the lamination member is formed of urine resist ink.

It may be desired that at least one of the layers of the lamination member disposed between the urine resist ink layer and the low and high resistance conductors is formed of solvent resist ink. The urine resist ink may be urethane combined ink of polyester polyal and isocyanate or UV hardened resin ink. The solvent resist ink may be a polyester resin ink.

The low and high resistance conductors may be formed by being printed with conductive ink including only conductive carbon as conductive substance.

Effects of the Invention

According to the present invention of the characters mentioned above, when the water (W) or like adheres between the exposure holes (6) in the current conduction state and the low resistance conductors (1,2) extending in parallel is then short-circuited, the current passing through the circuit increases in comparison with the case before the water (W) adhesion, so that the water content detection sensor can surely detect the water content (W) by observing the state of the circuit.

By printing the low and high resistance conductors on the film shaped carrier body or coating body, the water content detection sensor can be made thin, and hence, it can be disposed in a narrow portion or irregular surface portion.

By portions of the low resistance conductors corresponding to the exposure holes are formed as enlarged portions each having an area larger than that of the exposure hole, even in the case of fine low resistance conductors, the water content detection sensor having high precision can be provided.

In addition, since extending portions of the low resistance conductors and the exposure holes are formed to portions at which the water content is likely concentrated, the sensitivity of the water content detection sensor can be improved.

In the embodiment in which the through holes (9a,9b) are formed to the carrier body and the coating body, even in the case where the water exists on the side opposite to the exposure holes (6), the water content (W) can be exactly detected.

BRIEF DESCRIPTION OF THE INVENTION

Figure 1:
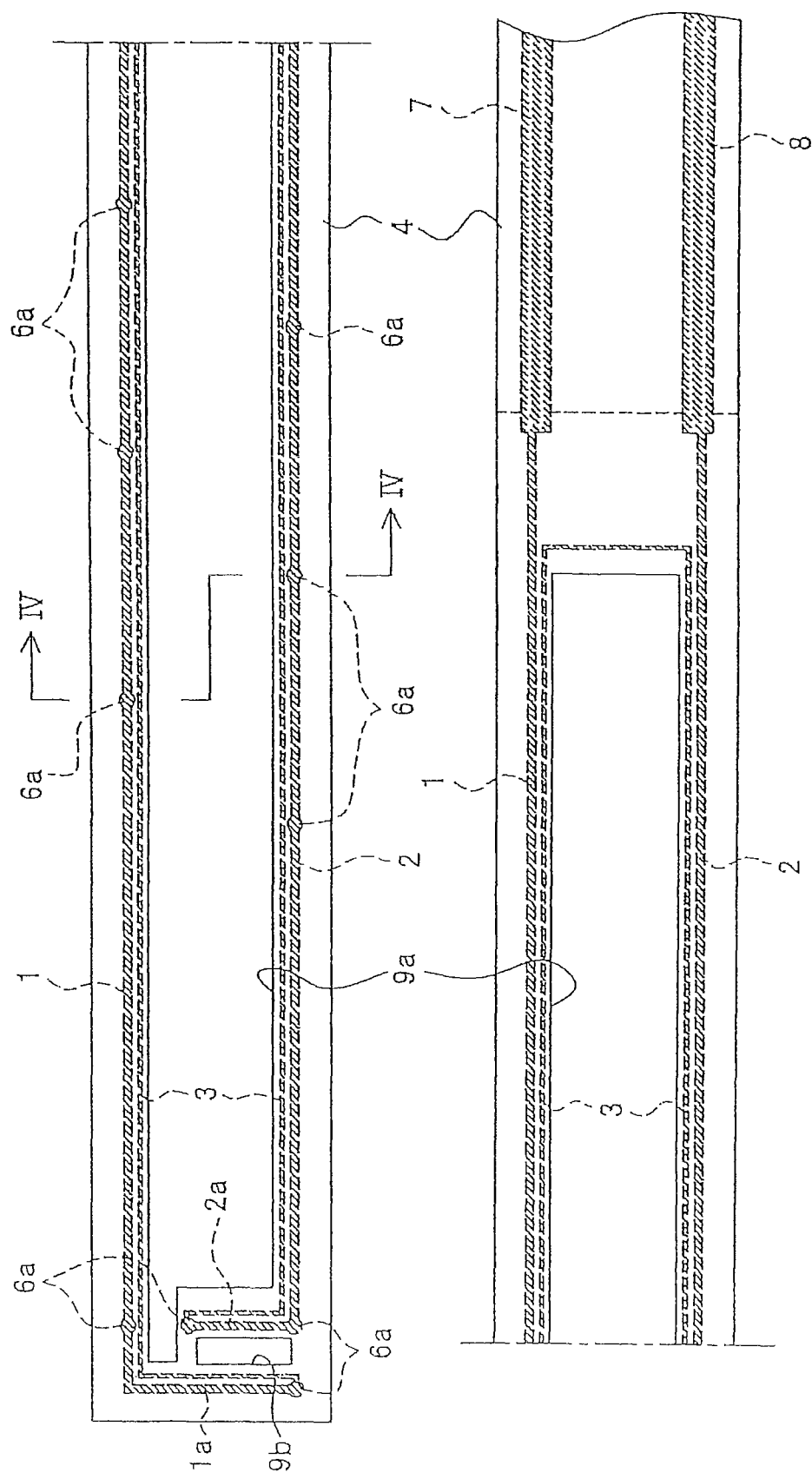
FIG. 1 is a front view of a water content detection sensor according to a first embodiment of the present invention.
Figure 2:
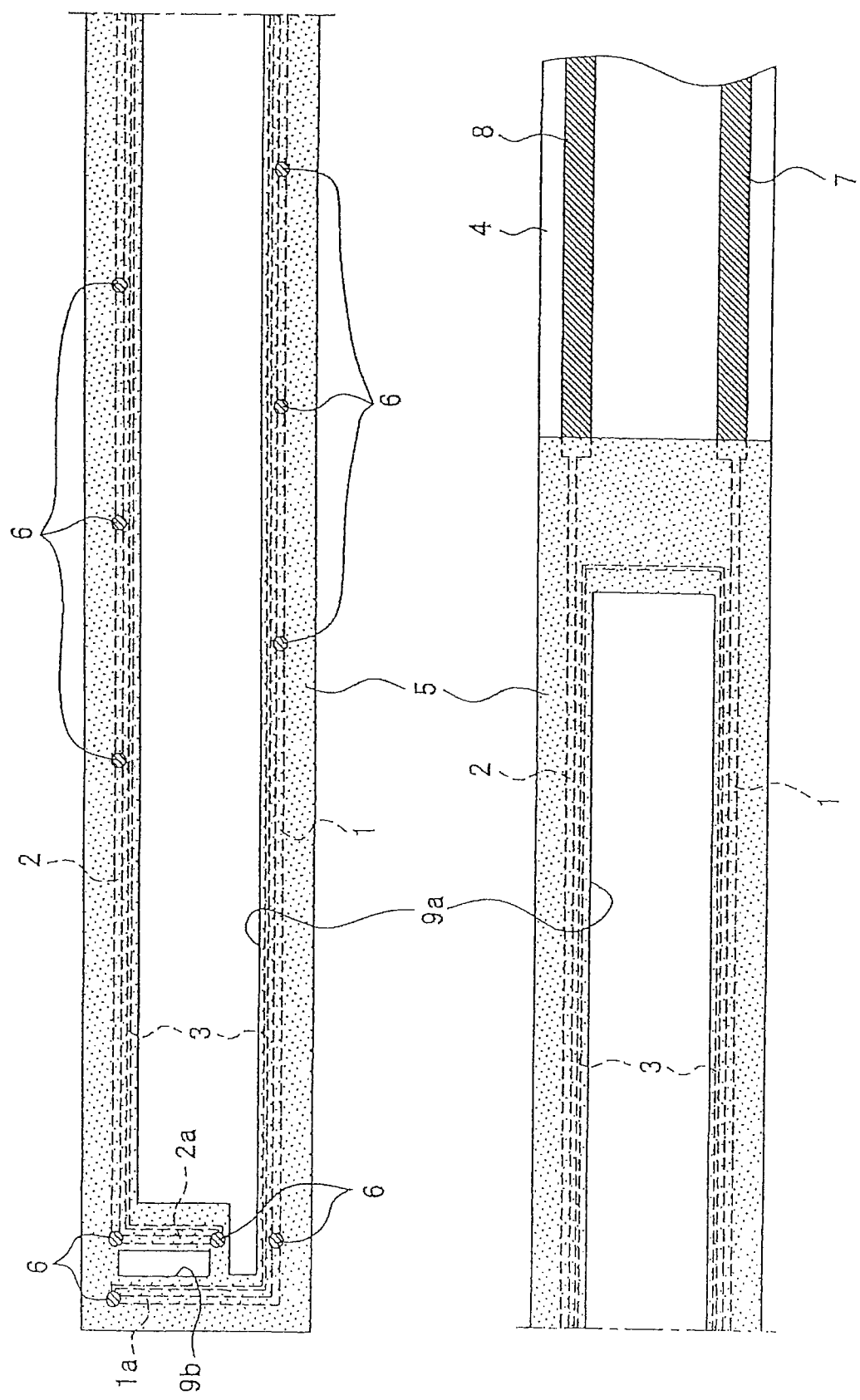
FIG. 2 is a rear view of the water content detection sensor of the first embodiment.
Figure 3:
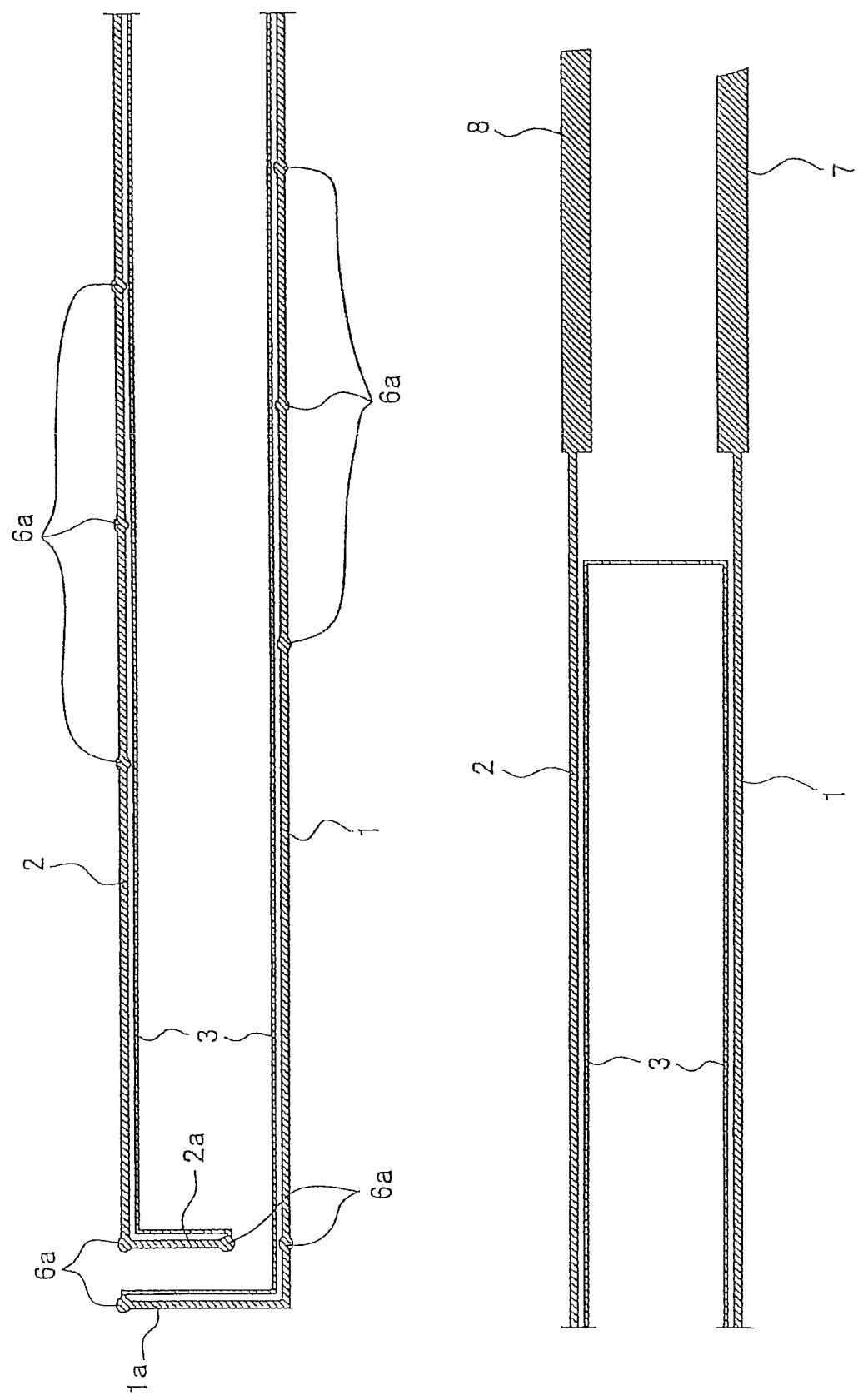
FIG. 3 is a plan view of a circuit member of the water content detection sensor.
Figure 4:
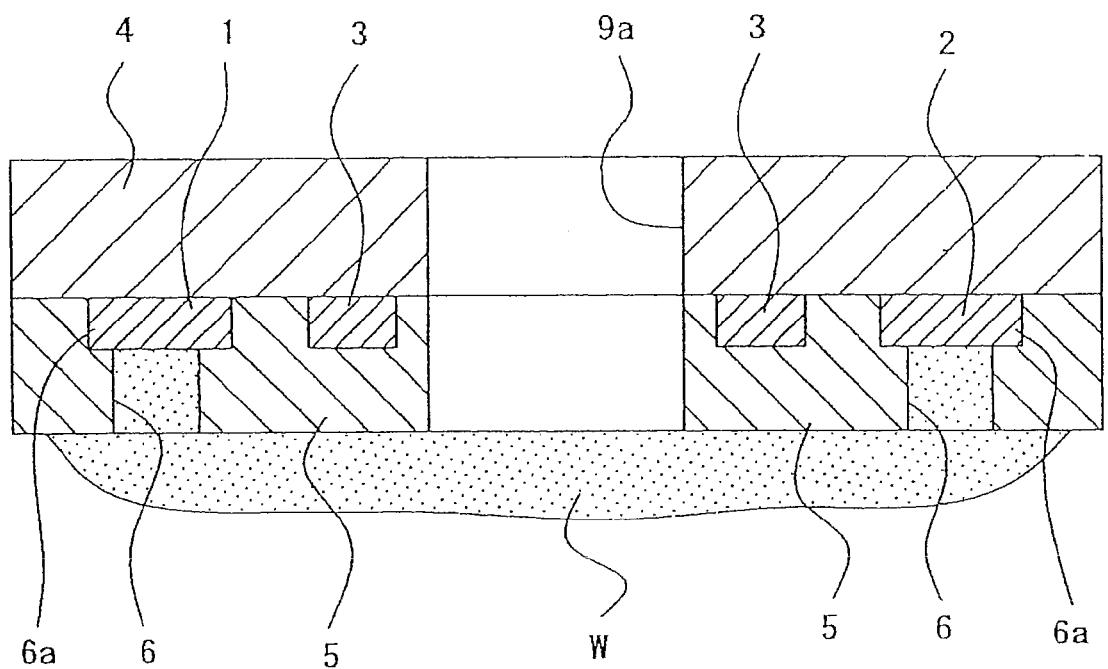
FIG. 4 is a sectional view taken along the line IV-IV in FIG. 1.

EXPLANATION OF REFERENCE NUMERAL 1, 2 . . . low resistance conductor 1a, 2a . . . extension portion, 3 . . . high resistance conductor, 4 . . . carrier body, 5 . . . coating body, 6 . . . exposure hole, 6a . . . enlarged portion, 9a, 9b . . . water passing holes 9a, W . . . water

BEST MODE FOR CARRYING OUT THE INVENTION

Hereunder, preferred embodiments of the present invention will be described with reference to the accompanying drawings.

First Embodiment

As shown in FIGS. 1 to 4, a water content (or merely water) detection sensor of this embodiment is provided with a circuit member including low resistance conductors 1, 2 extending in parallel and a high resistance conductor 3 connecting both ends of the low resistance conductors 1 and 2 so as to provide a series of line. The circuit member is interposed between a carrier or carrier body 4 and a coating body 5 both having water-proof property and insulating property, and the coating body 5 is formed with a plurality of holes as exposure holes 6 through which the low resistance conductors are exposed. The exposure holes 6 may be formed to the carrier body 4.

The carrier body or carrier 4 is formed into a bendable belt-shape and adapted to carry the entire structure of the water content detection sensor. The carrier body 4 has a water-proof property so as not to pass the water content and also has an electrically insulating property. In addition, it is desirable for the carrier body 4 to be formed to be transparent for the easy observation of the condition of the circuit member. The carrier body 4 is formed from a biaxially oriented film formed of polypropylene, polyethylene, polyvinyl-chloride, polyester, polyamide, polyimide, polycarbonate, polystyrene or like. It is also desirable for the carrier body 4 to have a thickness of 30 to 300 μm or, more preferably, 50 to 100 μm.

The circuit member includes the plural low resistance conductors 1 and 2, which extend in parallel along both the side edges of the belt-shaped film forming the carrier body 4. The low resistance conductors 1 and 2 are formed by printing the carrier body 4 with electrically conductive ink.

The conductive ink is formed by kneading binder, conductive metal powder and another filler, and as the binder, there may be used a polyvinyl chloride group resin, a polyacryl group resin, an epoxy group resin, a polyester group resin, polyacrylic urethane group resin, a polyolefin group resin, a urethane group resin, phenol or like resin.

As the conductive metal powder, there may be used silver, gold, copper, nickel, aluminium, conductive carbon or like.

The filler includes a viscosity controlling agent, a dispersing agent and the like.

The low resistance conductors 1 and 2 are formed by coating the conductive ink on the carrier body 4 in fine belt-like form through screen printing, direct gravure printing, flexographic printing or like printing process. Each of the low resistance conductors 1 and 2 is printed with such conductive ink so as to have, for example, a width of 1 mm, and a thickness of 10 μm, preferably, 5 to 30 μm. The resistances of these low resistance conductors 1 and 2 are made to be 0 to 200 kΩ, preferably, less than 100 kΩ by regulating the content of the conductive metal powder of the conductive ink. In this embodiment, it is set to be about 100 kΩ.

On the other hand, the high resistance conductor 3 in the circuit member is formed by being printed with the conductive ink of the composition substantially the same as that of the low resistance conductor 1 (2). However, less amount of the conductive metal powder is contained in the conductive ink, and as a result, the resistance value of the high resistance conductor 3 is set to be larger than that of the low resistance conductor 1 (2), for example, to several MΩ. In addition, in order to easily distinguish from the low resistance conductors 1 and 2, the high resistance conductor 3 is formed to have a fine shape having thickness of, for example, 0.5 mm. Furthermore, the high resistance conductor 3 extends, from one end of one of the low resistance conductors 1, to the other end along this low resistance conductor 1, then to other one end of the other low resistance conductor 2 and further toward one end of this low resistance conductor 2 therealong. As a result, the high and low resistance conductors 3, 1 and 2 are connected in form of a series of line on the carrier body 4 as one conductor, and a potential difference is caused between the rear end portions of the low resistance conductors 1 and 2 so that the electric current of a constant rate passes. It is desirable for the high resistance conductor 3 to have a resistance value of 1 to 10 MΩ, preferably of 2 to 6 MΩ.

Lead wires 7 and 8 are connected to the other ends of the two low resistance conductors 1 and 2, respectively. These lead wires 7 and 8 are also formed by being printed on the carrier body 4 with the conductive ink, which is the same as or similar to that for the low resistance conductors 1 and 2.

The low resistance conductors 1 and 2 have extensions 1a and 2a to the front end portion of the carrier 4, for example, on which the water content is likely concentrated. More specifically, one ends of the respective low resistance conductors 1 and 2 extend, in a bend form, to the opposing side low resistance conductors 2 and 1 so as to cross the carrier body 4.

Further, the high resistance conductor 3 is also bent and extend as like as the low resistance conductors 1 and 2.

The coating body 5 is coated on the surface of the carrier body 4 from the upper portion of the circuit member so as to insulate the circuit member together with the carrier body 4. The coating body is formed of the printing ink.

The printing ink is formed by kneading a binder, pigment and other fillers.

As the binder, there may be used a polyvinyl chloride group resin, polyacrylic group resin, epoxy group resin, polyester group resin, polyacrylic urethane group resin, polyolefin group resin, polyurethane group resin, or phenol group resin. The binder further formed through urethane-coupling of polyester polyal and isocyanate or UV hardened resin.

As the pigment, there may be used a white pigment, for example, for easy identification from the circuit. Further, the filler may include a viscosity controlling agent, dispersing agent and the like.

Such printing ink is coated on the surface of the carrier above the circuit member, through the screen printing, direct gravure printing process or like, with the lead wires 7 and 8 remaining uncoated, thus providing the coating body 5. This coating (coated) body 5 serves as insulating film and waterproof film.

A plurality of exposure holes 6 are formed on the coating body 5 at which the low resistance conductors 1 and 2 are exposed. These exposure holes 6 are formed at the same time as the printing time of the coating body 5. In the illustrated example, these exposure holes 6 are formed at a predetermined interval along the two low resistance conductors 1 and 2 extending in parallel, and one or plural exposure holes 6 are also formed to the extending portions 1a and 2a. In the illustrated example, each of the exposure holes 6 also has a circular shape, but it may take elliptical shape, rectangular shape or like shape as occasion demands.

Further, an enlarged portion 6a having an area larger than the exposure hole 6 may be formed, as occasion demands, on the low resistance conductor 1 (2) corresponding to the exposure hole 6. According to the formation of such enlarged portion 6a, even if the exposure hole 6 is formed in a manner slightly offset, the low resistance conductors 1 and 2 can be exposed properly. When water content or water W adheres so as to straddle on or bridge between the exposure holes 6 on the low resistance conductors, electric current is short-circuited between the low resistance conductors 1 and 2, and this current value is larger than the case of no short-circuited state, thus detecting the adhesion of the water W.

The carrier body 4 is formed with water passing holes 9a penetrating the carrier 4. In the illustrated example, such water passing hole 9 is perforated into approximately rectangular shape between the low resistance conductors 1 and 2 or between the extended portions 1a and 1b, but it may be perforated as an aggregation of many perforations. Accordingly, even in the case where the water content W adheres on the side of the coating body 5, it passes through the water passing holes 9a and 9b to the exposure hole side to thereby properly detect the water content W.

Hereunder, the functions of the water content detection sensor of the structure mentioned above will be described.

The circuit member and the coating body 5 of the water content detection sensor are printed, with different colors of inks, on the carrier body 4 formed from a transparent film, so that the presence of disconnection (breaking of wire) of the circuit or presence of fault of the coating body 5 can be immediately visually observed, thus easily discriminating the performance of the water content detection sensor itself.

Incidentally, when the lead wires 7 and 8 are connected to a power source, not shown, to thereby apply a voltage on the circuit member, the current passes from one of the low resistance conductor 1 to the other low resistance conductor 2 through the high resistance conductor 3. By detecting this current, the performance of the water content detection sensor can be judged.

The water content detection sensor is used in a manner that it is bonded on a vehicle body, a window glass or others of an automobile so that the exposure hole side is exposed outward, or it may be bonded to a diaper.

When the lead wires 7 and 8 are connected to the power source such as battery so as to apply voltage to the circuit member, the current passes from one of the low resistance conductor 1 to the other low resistance conductor 2 through the high resistance conductor 3. By detecting this current, it is judged whether the water content detection sensor operates normally or not.

When the water content W of, for example, rainwater, adheres so as to straddle the exposure hole 6 on the two low resistance conductors 1 and 2, they are short-circuited and the current passes. This current is larger than that in the case of no short-circuited state, and hence, by detecting this current value, the adhesion of the water content can be detected. This detection is informed to a control section of the automobile by transmitting a signal from the detection sensor and, then, the control section judges the fact of presence of rainfall and then instructs so as to operate wipers. After the rainfall, the water content of the rainwater is evaporated, the current value is decreased, and by discriminating this fact, the control section stops the operation of the wipers.

In the case of the diaper, when discharged urination adheres so as to bridge across the exposure hole 6 on the low resistance conductors 1 and 2, the conductors are short-circuited and the electric current passes therebetween. By detecting this fact, the presence of the urination is informed through an alarm, for example.

Second Embodiment

Figure 5:
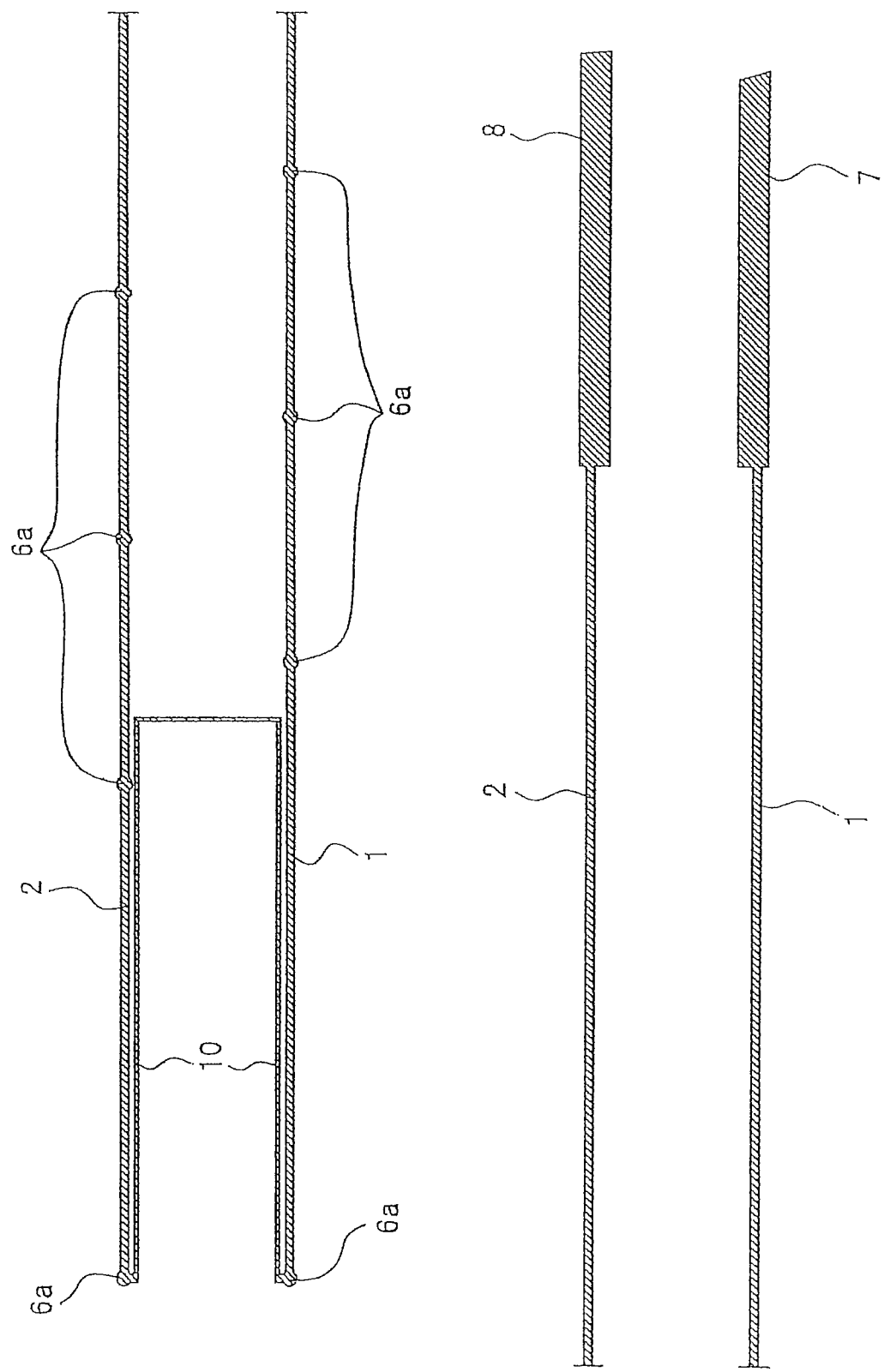
FIG. 5 is a plan view showing a circuit member of a water content detection sensor according to a second embodiment of the present invention.

In this second embodiment, as shown in FIG. 5, a high resistance conductor 10 in the circuit member of the water content detection sensor is made short in comparison with that of the first embodiment.

Further, in this second embodiment, the same reference numerals are added to members or elements corresponding to those in the first embodiment and duplicated explanation is omitted herein.

Third Embodiment

Figure 6:
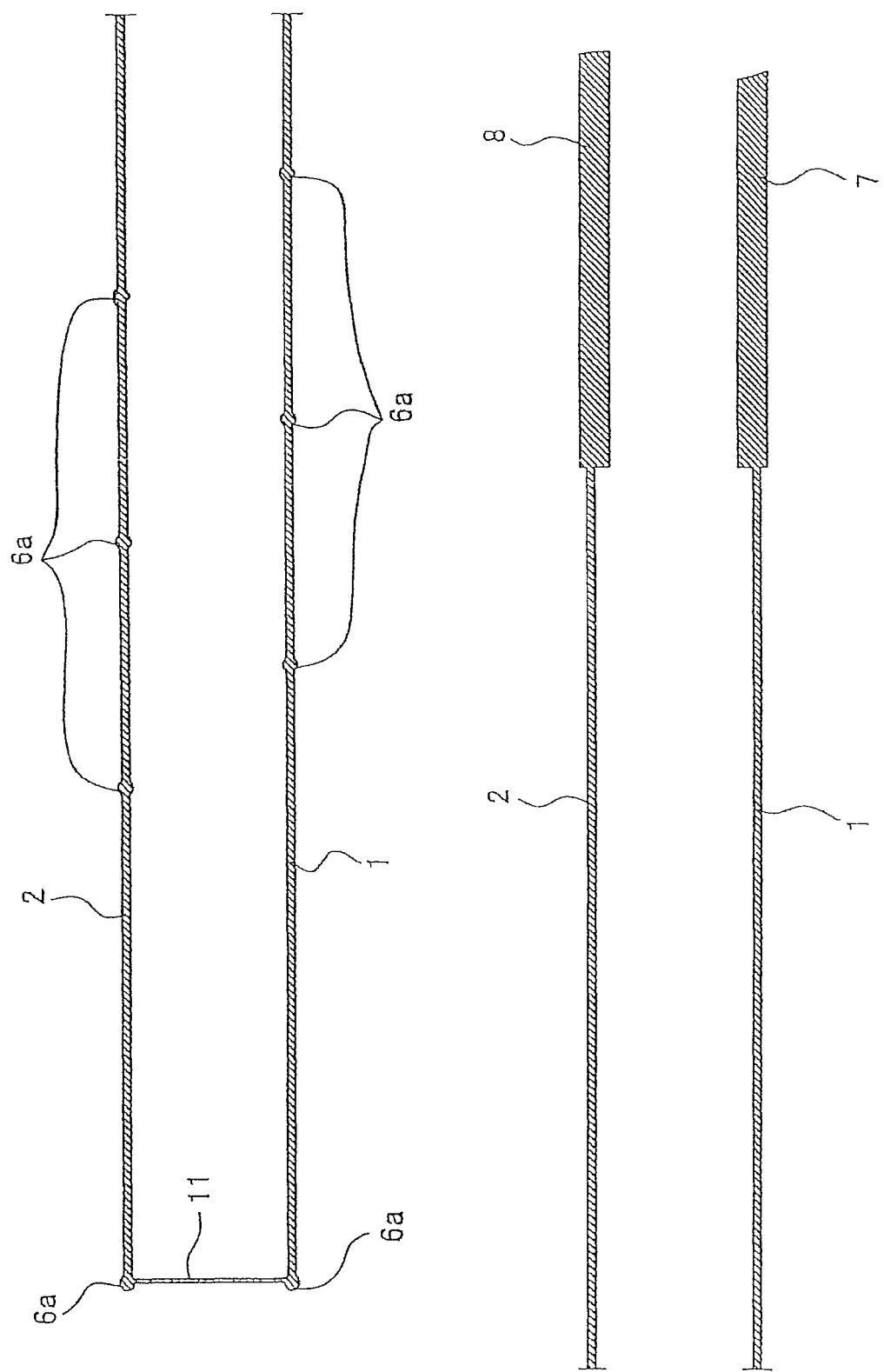
FIG. 6 is a plan view showing a circuit member of a water content detection sensor according to a third embodiment of the present invention.

In this third embodiment, as shown in FIG. 6, a high resistance conductor 11 in the circuit portion of the water content detection sensor is made further short in comparison with those of the first and second embodiments so as to extend linearly between two low resistance conductors 1 and 2.

Further, in third embodiment, the same reference numerals are added to members or elements corresponding to those in the first or second embodiment and duplicated explanation is omitted herein.

Fourth Embodiment

Figure 7:
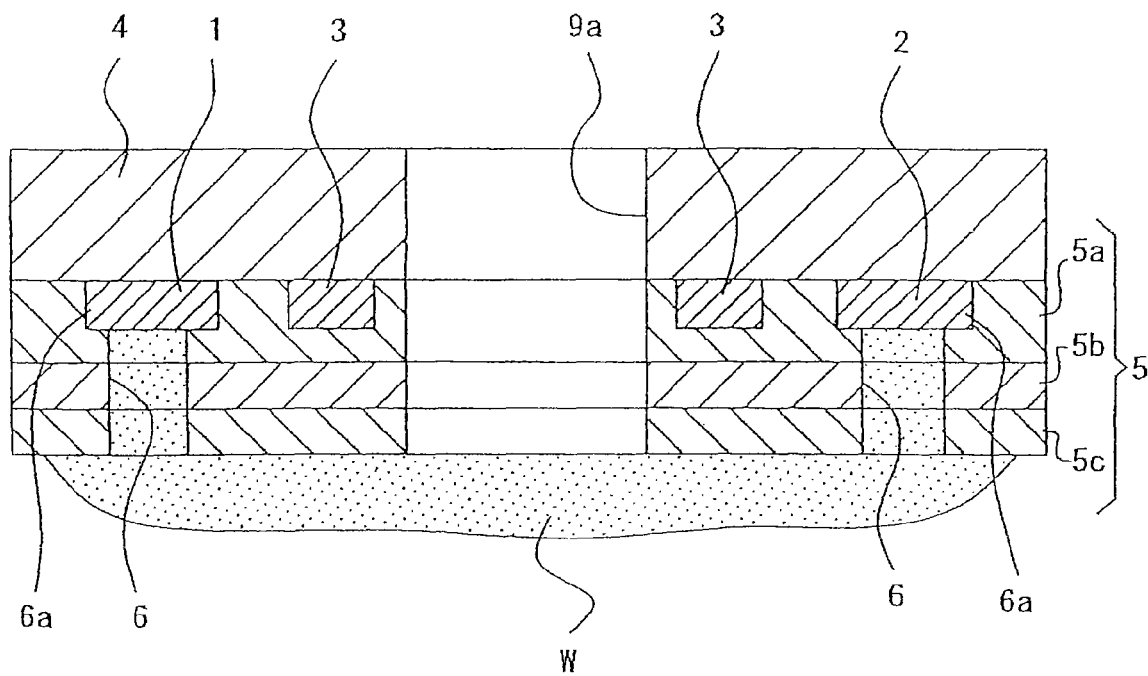
FIG. 7 is a sectional view, like that of FIG. 4, of a water content detection sensor according to a fourth embodiment of the present invention.

In a water content detection sensor of this fourth embodiment, as shown in FIG. 7, the coating body 5 formed to the exposure hole 6 is formed as a lamination member of a printed ink layer. More specifically, the lamination member of the coating body includes three printing ink layers such that a first solvent resist ink layer 5a is printed on the low and high resistance conductors 1, 2 and 3 of the circuit member of the surface of the carrier body 4, an urine resist ink layer 5b is printed on the first layer 5a and a second solvent resist ink layer 5c is printed further on the urine resist ink layer 5b. In the printing operations of the respective layers, the exposure holes 6 are simultaneously formed as non-printed portion.

Polyester resin ink will be used as the solvent resist ink, and as the urine resist ink, there will be used urethane combined ink of polyester polyal and isocyanate, or UV hardened resin ink.

In the case of application of the water content detection sensor to the diaper, since the low and high resistance conductors 1, 2 and 3 are protected by the coating body 5 consisting of the multi-layers of the printing ink layers 5*a* to 5*c*, the intrusion of the urination from the urine resist ink layer 5*b* into the low and high resistance conductors 1, 2 and 3 can be prevented. Accordingly, the low and high resistance conductors at the circuit member can be also prevented from changing in the resistance values thereof. As a result, urination can be properly detected in a plurality of times and the diaper can be used for the plural urinations. The invasion of the solvent component of the urine resist ink layer 5*b* into the circuit member can be shut off by the first solvent resist ink layer 5*a*, and the invasion on the side opposite to the circuit portion can be also shut off by the second solvent resist ink layer 5*c*.

Further, in this fourth embodiment, the same reference numerals are added to members or elements corresponding to those in the first to third embodiment and duplicated explanation is omitted herein.

Fifth Embodiment

In the water content detection sensor of the fifth embodiment, the low and high resistance conductors 1, 2 and 3 in the first to fourth embodiments is printed with a conductive ink including only conductive carbon as conductive substance. Accordingly, the low and high resistance conductors 1, 2 and 3 exhibit high resistance against urine component, and hence, the variation of the resistance value can be suppressed. As a result, in the case when such water content detection sensor is applied to the diaper, the urination can be properly detected in plural times.

It is to be noted that the present invention is not limited to the described embodiments and many other changes and modifications may be made without departing from the scopes of the appended claims. For example, the exposure holes may be formed to the carrier body instead of the coating body. In addition, the coating body is formed with the printing ink layers, but it may be formed with a film member as like as the carrier body.

The invention claimed is:

1. A water content detection sensor comprising:
a circuit member in which low resistance conductors disposed in parallel to each other and a high resistance conductor connecting end portions of the respective low resistance conductors;
a carrier body having a water-proof property and an insulating property; and
a coating body having a water-proof property and an insulating property, the circuit member being disposed between the carrier body and the coating body,
wherein a plurality of exposure holes are formed to the carrier body or the coating body so as to expose the low resistance conductors at plural portions, and when water content adheres between the exposure holes and the low resistance conductors are then short-circuited in a current conduction state, a current value is made larger than that before the water content adheres, and
the coating body and the carrier body to which the exposure holes are formed as part of a lamination member composed of printing ink layers with at least one layer of the lamination member being formed of urine resist ink and at least one layer of the lamination member disposed between the urine resist ink layer and the low and high resistance conductors being formed of a solvent resist ink.

2. The water detection sensor according to claim 1, wherein the low resistance conductors and the high resistance conductor are formed by being printed on the carrier body in form of film and the coating body is printed thereon.

3. The water detection sensor according to claim 1, wherein portions of the low resistance conductors corresponding to the exposure holes are formed as enlarged portions each having an area larger than that of the exposure hole.

4. The water content detection sensor according to claim 1, wherein extending portions of the low resistance conductors and the exposure holes are formed to portions at which the water content is likely concentrated.

5. The water content detection sensor according to claim 1, wherein the carrier body and the coating body are formed with through holes through which water passes.

6. The water content detection sensor according to claim 1, wherein the low resistance conductors and the high resistance conductor are printed with conductive ink including conductive carbon.

7. The water content detection sensor according to claim 6, wherein the printing ink of the low resistance conductor includes the conductive carbon of an amount larger than that included in the printing ink of the high resistance conductor.

8. The water content detection sensor according to claim 1 wherein the solvent resist ink is a polyester resin ink.

9. The water content detection sensor according to claim 1 wherein the urine resist ink is urethane combined ink of polyester polyal and isocyanate or UV hardened resin ink.

10. The water content detection sensor according to claim 1, wherein the low and high resistance conductors are formed by being printed with conductive ink including only conductive carbon as conductive substance.

* * * * *